US012221552B2

(12) United States Patent
Knight et al.

(10) Patent No.: US 12,221,552 B2
(45) Date of Patent: Feb. 11, 2025

(54) WATER-SOLUBLE COATINGS FOR SUBSTRATE SURFACES

(71) Applicant: MONOSOL, LLC, Merrillville, IN (US)

(72) Inventors: Jonathon Knight, Laporte, IN (US); Hao Chang, Bethel, CT (US)

(73) Assignee: MONOSOL, LLC, Merrillville, IN (US)

( * ) Notice: Subject to any disclaimer, the term of this patent is extended or adjusted under 35 U.S.C. 154(b) by 711 days.

(21) Appl. No.: 17/428,748

(22) PCT Filed: Feb. 6, 2020

(86) PCT No.: PCT/US2020/016907
§ 371 (c)(1),
(2) Date: Aug. 5, 2021

(87) PCT Pub. No.: WO2020/163546
PCT Pub. Date: Aug. 13, 2020

(65) Prior Publication Data
US 2022/0127488 A1    Apr. 28, 2022

Related U.S. Application Data

(60) Provisional application No. 62/801,949, filed on Feb. 6, 2019.

(51) Int. Cl.
| | | |
|---|---|---|
| C09D 129/04 | (2006.01) | |
| B05D 7/00 | (2006.01) | |
| C08F 116/06 | (2006.01) | |
| C08F 120/06 | (2006.01) | |
| C08K 5/00 | (2006.01) | |
| C08K 5/053 | (2006.01) | |
| C08K 5/105 | (2006.01) | |
| C08K 5/20 | (2006.01) | |
| C09D 133/02 | (2006.01) | |
| H01M 50/124 | (2021.01) | |
| H01M 50/126 | (2021.01) | |

(52) U.S. Cl.
CPC .......... *C09D 129/04* (2013.01); *B05D 7/52* (2013.01); *C08F 116/06* (2013.01); *C08F 120/06* (2013.01); *C08K 5/0041* (2013.01); *C08K 5/053* (2013.01); *C08K 5/105* (2013.01); *C08K 5/20* (2013.01); *C09D 133/02* (2013.01); *H01M 50/124* (2021.01); *H01M 50/126* (2021.01); *B05D 2202/00* (2013.01)

(58) Field of Classification Search
CPC .... C09D 129/04; C09D 133/02; C09D 5/008; C09D 11/328; C09D 11/38; C09D 11/322; C09D 7/41; C09D 7/61; B05D 7/52; B05D 2202/00; C08F 116/06; C08F 120/06; C08K 5/0041; C08K 5/053; C08K 5/105; C08K 5/20; H01M 50/124; H01M 50/126; H01M 50/1245; C07C 63/08; B32B 2250/02; B32B 2307/7166; B32B 27/08; B32B 27/18; B32B 27/20; B32B 27/306; B32B 27/308; C11D 17/042; C08L 33/02; C08L 29/04
USPC ........................................................ 524/503
See application file for complete search history.

(56) References Cited

U.S. PATENT DOCUMENTS

| | | |
|---|---|---|
| 3,350,285 A | 10/1967 | Nishigaki et al. |
| 3,383,211 A | 5/1968 | Poels et al. |
| 3,418,219 A | 12/1968 | Fahlbusch |
| 3,664,961 A | 5/1972 | Norris |
| 3,696,498 A | 10/1972 | Leontaritis et al. |
| 3,767,449 A | 10/1973 | Hayashi et al. |
| 3,919,678 A | 11/1975 | Penfold |
| 3,929,678 A | 12/1975 | Laughlin et al. |
| 3,975,280 A | 8/1976 | Hachmann et al. |
| 4,000,093 A | 12/1976 | Nicol et al. |
| 4,033,918 A | 7/1977 | Hauber |
| 4,075,116 A | 2/1978 | Mesaros |
| 4,222,905 A | 9/1980 | Cockrell, Jr. |
| 4,239,659 A | 12/1980 | Murphy |
| 4,246,612 A | 1/1981 | Berry et al. |
| 4,259,217 A | 3/1981 | Murphy |
| 4,692,494 A * | 9/1987 | Sonenstein ............. C08L 33/02 524/388 |
| 4,719,038 A | 1/1988 | Sobata et al. |
| 4,748,049 A | 5/1988 | Charles et al. |
| 4,810,410 A | 3/1989 | Diakun et al. |
| 5,114,611 A | 5/1992 | Van Kralingen et al. |
| 5,137,646 A | 8/1992 | Schmidt et al. |
| 5,227,084 A | 7/1993 | Martens et al. |
| 5,340,496 A | 8/1994 | Sato et al. |
| 5,576,281 A | 11/1996 | Bunch et al. |
| 6,599,871 B2 | 7/2003 | Smith |
| 6,660,708 B2 | 12/2003 | Kaess |
| 7,297,205 B2 | 11/2007 | Michl et al. |
| 8,288,332 B2 | 10/2012 | Fossum et al. |

(Continued)

FOREIGN PATENT DOCUMENTS

| | | |
|---|---|---|
| CA | 3047026 A1 | 6/2018 |
| CN | 102746462 A | 10/2012 |

(Continued)

OTHER PUBLICATIONS

International Application No. PCT/US2020/016907, International Preliminary Report on Patentability, mailed Aug. 10, 2021.

(Continued)

*Primary Examiner* — Hannah J Pak
(74) *Attorney, Agent, or Firm* — MARSHALL, GERSTEIN & BORUN LLP (57) ABSTRACT

Disclosed herein are coating compositions and/or coatings comprising a water-soluble resin mixture comprising a polyvinyl alcohol (PVOH) and a polyacrylic acid (PAA), and further comprising a colorant and/or an aversive agent, surfaces of substrates coated with the compositions, and methods of making and using the same.

28 Claims, 1 Drawing Sheet

(56) References Cited

U.S. PATENT DOCUMENTS

| | | |
|---|---|---|
| 8,835,372 B2 | 9/2014 | Jennewein |
| 9,865,862 B2 | 1/2018 | Ok |
| 9,959,985 B2 | 5/2018 | Ichinomiya et al. |
| 10,240,114 B2 | 3/2019 | Labeque et al. |
| 2002/0025411 A1 | 2/2002 | Chung |
| 2003/0060390 A1 | 3/2003 | Demeyere et al. |
| 2003/0126282 A1 | 7/2003 | Sarkar et al. |
| 2003/0139312 A1 | 7/2003 | Caswell et al. |
| 2004/0204337 A1 | 10/2004 | Corona et al. |
| 2005/0181003 A1 | 8/2005 | Endepols et al. |
| 2007/0219111 A1 | 9/2007 | Ward et al. |
| 2007/0266901 A1* | 11/2007 | Rance ............... C08L 3/02 106/501.1 |
| 2009/0298739 A1 | 12/2009 | Courchay et al. |
| 2010/0062340 A1 | 3/2010 | Ide |
| 2010/0105801 A1 | 4/2010 | Choi |
| 2012/0164424 A1 | 6/2012 | Vicari et al. |
| 2013/0240388 A1 | 9/2013 | Koch et al. |
| 2014/0162929 A1 | 6/2014 | Labeque et al. |
| 2015/0158645 A1 | 6/2015 | Meier et al. |
| 2016/0102278 A1* | 4/2016 | Labeque ............ C11D 17/043 510/513 |
| 2016/0185994 A1* | 6/2016 | Peet ................. C09D 109/08 524/522 |
| 2017/0067000 A1 | 3/2017 | Brandt-Sanz et al. |

FOREIGN PATENT DOCUMENTS

| | | |
|---|---|---|
| CN | 105440531 A | 3/2016 |
| CN | 105997918 A | 10/2016 |
| CN | 106752467 A | 5/2017 |
| CN | 106752709 A | 5/2017 |
| CN | 106795306 A | 5/2017 |
| CN | 107022212 A | 8/2017 |
| CN | 107033714 A | 8/2017 |
| CN | 107446431 A | 12/2017 |
| EA | 012372 B1 | 10/2009 |
| EP | 0197434 B1 | 7/1989 |
| EP | 0414549 A2 | 2/1991 |
| EP | 507402 A1 | 10/1992 |
| EP | 2088187 A1 | 8/2009 |
| EP | 2258820 A1 | 12/2010 |
| EP | 2889335 A1 | 7/2015 |
| EP | 3138901 A1 | 3/2017 |
| EP | 2619826 B1 | 1/2018 |
| FR | 2666348 A1 | 3/1992 |
| FR | 2666349 A1 | 3/1992 |
| GB | 604749 A | 7/1948 |
| GB | 753050 A | 7/1956 |
| GB | 769271 A | 3/1957 |
| GB | 854346 A | 11/1960 |
| GB | 994062 A | 6/1965 |
| GB | 1137741 A | 12/1968 |
| GB | 1339435 A | 12/1973 |
| GB | 1466799 A | 3/1977 |
| GB | 2090603 A | 7/1982 |
| JP | H05185550 A | 7/1993 |
| JP | 2967855 B2 | 10/1999 |
| JP | 2001105529 A | 4/2001 |
| JP | 2006077129 A | 3/2006 |
| JP | 2007256685 A | 10/2007 |
| JP | 2009034589 A | 2/2009 |
| JP | 2013537904 A | 10/2013 |
| JP | 2016108426 A | 6/2016 |
| JP | 2016222879 A | 12/2016 |
| JP | 2019-019114 A | 2/2019 |
| RU | 2324349 C2 | 5/2008 |
| RU | 2359366 C1 | 6/2009 |
| WO | WO-93/08874 A1 | 5/1993 |
| WO | WO-93/08876 A1 | 5/1993 |
| WO | WO-94/004656 A2 | 3/1994 |
| WO | WO-94/22800 A1 | 10/1994 |
| WO | WO-2009/152031 A1 | 12/2009 |
| WO | WO-2012039632 A2 | 3/2012 |
| WO | WO-2014030208 A1 | 2/2014 |

OTHER PUBLICATIONS

International Application No. PCT/US2020/016907, International Search Report and Written Opinion, mailed Jul. 16, 2020.

Mahabadi et al., Molecular weight—viscosity relationships for a broad molecular weight distribution polyer, Can. J. Chem., 63:221 (1985).

Standard Test Methods for Measuring Adhesion by Tape Test, ASTM Designation: D3359-09 (2009).

Wang et al., Highly Stretchable Free-Standing Poly(acrylic acid)-block-poly(vinyl alcohol) Films Obtained from Cobalt-Mediated Radical Polymerization, Macromolecules, 50(16):6054-63 (2017).

Lakokraska, "Interior acrylic paint VD-AK-2180", Mar. 9, 2017 Retrieved from the Internet at: <URL:https://lakokraska-ya.ru/kraska-interernaya-akrilovaya-vd-ak-1179-dlya-detskoi-komnaty> (2023).

* cited by examiner

WATER-SOLUBLE COATINGS FOR SUBSTRATE SURFACES

FIELD OF THE INVENTION

The present disclosure relates generally to coating compositions and related articles. More particularly, the disclosure relates to coating compositions for water-soluble coatings suitable for adhering to substrate surfaces.

BACKGROUND

Water-soluble polymeric resins have been used for coating substrates to protect the substrate from damage, for making films to carry a chemical, for making films to timely release a chemical, or a combination thereof.

SUMMARY

One aspect of the disclosure provides a coating composition comprising a water-soluble resin mixture, the water-soluble resin mixture comprising (a) a polyvinyl alcohol (PVOH) and a polyacrylic acid (PAA) and (b) a colorant.

Another aspect of the disclosure provides a coating composition comprising a water-soluble resin mixture, the water-soluble resin mixture comprising (a) a PVOH and a PAA and (b) an aversive agent.

Another aspect of the disclosure provides a coating comprising a first water-soluble layer, the first water-soluble layer comprising a dried first coating composition according to the disclosure.

Another aspect of the disclosure provides a method for applying the coating composition according to the disclosure herein to a surface of a substrate, e.g. a metal surface, the method comprising contacting the surface of the substrate with the coating composition.

Another aspect of the disclosure provides a method of deterring ingestion of a substrate comprising applying to a surface of the substrate the coating composition according to the disclosure.

Another aspect of the disclosure provides an article comprising a surface on a substrate, the surface comprising a coating according to the disclosure.

Another aspect of the disclosure herein is a kit comprising a substrate having a surface coated with the dried coating composition described herein and instructions to not wash, rinse, or otherwise contact the substrate surface with water or solvents.

In any method or article described herein, the surface can be a metal surface.

Further aspects and advantages will be apparent to those of ordinary skill in the art from a review of the following detailed description. While the coating composition, coating, water-soluble resin mixture, article, kit, and the methods are susceptible of embodiments in various forms, the description hereafter includes specific embodiments with the understanding that the disclosure is illustrative, and is not intended to limit the invention to the specific embodiments described herein.

DETAILED DESCRIPTION

In the disclosure presented herein, one aspect provides a coating composition comprising a water-soluble resin mixture, the water-soluble resin mixture comprising a polyvinyl alcohol (PVOH), a polyacrylic acid (PAA), and a colorant, wherein the colorant is at a concentration±10% of the saturation point of the colorant. Another aspect of the disclosure provides a coating composition comprising a water-soluble resin mixture, the water-soluble resin mixture comprising a PVOH, a PAA, and an aversive agent. In embodiments, the coating composition comprises the PVOH and PAA in a ratio in a range of 90:10 to 10:90 by weight, respectively. In embodiments, the PAA of the coating composition can have a weight average molecular weight ($\overline{M}w$) in a range of 1000 Da to 300,000 Da. In embodiments, the PAA of the coating composition can be a homopolymer.

The coating compositions according to the disclosure can be designed to provide one or more advantages, for example, (a) excellent adhesion to substrate surfaces, e.g. metal surfaces, as characterized by an adhesion value of 3 or greater according to the Adhesion Test described herein, (b) child safety features, such as, for example rapid transfer of aversive agents, high colorant content to a soft tissue environment such as, lips, cheeks, tongue, or a combination thereof, (c) resistance to easy colorant transfer to wet or moist hands, (d) deterring ingestion of a substrate, or a combination thereof.

Another aspect of the disclosure provides a coating, comprising a first water-soluble layer, the first water-soluble layer comprising a dried first coating composition according to the disclosure herein. In embodiments, the coating further comprises a second water-soluble layer, the second water-soluble layer comprising a dried second coating composition. In embodiments, the second coating composition is free of a colorant. In embodiments, the second coating composition comprises a water-soluble polymer. In embodiments, the water-soluble polymer of the second coating composition comprises PVOH. In embodiments, the PVOH of the second coating composition can have a viscosity of no more than 10 cP in a 4% aqueous solution at 20° C. In embodiments, the PVOH of the second coating composition can have a degree of hydrolysis in a range of about 85% to about 95%. In embodiments, the PVOH of the second coating composition can have a degree of hydrolysis of about 88%.

The coating according to the disclosure can be designed to provide one or more advantages, (a) excellent adhesion to substrate surfaces as characterized by an adhesion value of 3 or greater according to the Adhesion Test described herein, (b) child safety features, such as, for example rapid transfer of aversive agents, high colorant content to a soft tissue environment such as, lips, cheeks, tongue, or a combination thereof, (c) resistance to easy colorant transfer to wet or moist hands, (d) deterring ingestion of a substrate, or a combination thereof.

To be considered a water-soluble layer according to the present disclosure, the layer, at a thickness of about 0.1 mil to about 5 mil, has an average percent dissolution of at least 8, in accordance with the Dissolution Test described below. The term "water-soluble polymer" herein refers to a polymer that has a percent dissolution of 8 or more according to the Dissolution Test, described below.

All percentages, parts and ratios referred to herein are based upon the total dry weight of the coating composition of the present disclosure and all measurements made are at about 25° C., unless otherwise specified. All such weights as they pertain to listed ingredients are based on the ingredient level and therefore do not include carriers or by-products that may be included in commercially available materials, unless otherwise specified.

All ranges set forth herein include all possible subsets of ranges and any combinations of such subset ranges. By default, ranges are inclusive of the stated endpoints, unless stated otherwise. Where a range of values is provided, it is understood that each intervening value between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also contemplated to be part of the disclosure.

It is expressly contemplated that for any number value described herein, e.g. as a parameter of the subject matter described or part of a range associated with the subject matter described, an alternative which forms part of the description is a functionally equivalent range surrounding the specific numerical value (e.g. for a dimension disclosed as "40 mm" an alternative embodiment contemplated is "about 40 mm").

As used herein and unless specified otherwise, the terms "wt. %" and "wt %" are intended to refer to the composition of the identified element in "dry" (non-water) parts by weight of the entire coating composition and coating, as the case may be depending on context.

As used herein and unless specified otherwise, the term "PHR" ("phr") is intended to refer to the composition of the identified element in parts per one hundred parts water-soluble polymer resin(s) (whether PVOH or in combination with one or more other polymer resins).

The coating compositions described herein can comprise a water-soluble resin mixture, and the water-soluble resin mixture can comprise a PVOH and a PAA. The term "water-soluble resin mixture" herein refers to a resin mixture that has a percent dissolution of 8 or more according to the Dissolution Test, described below. The PVOH and PAA can be present in a ratio in a range of 99:1 to 1:99 by weight, respectively. In embodiments, the PVOH and PAA can be present in a ratio in a range of 95:5 to 5:95 or 90:10 to 10:90 by weight, respectively. In embodiments, the PVOH and PAA are present in a ratio in a range of 99:1 to 20:80 by weight, respectively, such as 95:5, 90:10, 85:15, 80:20, 75:25, 70:30, 65:35, 60:40, 55:45, 50:50, 45:55, 40:60, 35:65, 30:70, 25:75, or 20:80 by weight, respectively. In various embodiments, the PVOH and PAA are present in a ratio in a range of 80:20 to 20:80 by weight, respectively.

As described herein, the combination of PVOH and PAA advantageously provides a synergistic adhesion to a substrate surface when blended. For example, when either PVOH or PAA is used as the sole resin in a coating composition, the coating composition generally shows relatively low adhesion to a metal surface of a substrate, such as a battery. As used herein, and unless defined otherwise, "low adhesion" or "poor adhesion" refers to an adhesion value of less than or equal to 2, according to the Adhesion Test described herein. However, as demonstrated herein, adhesion to a surface of a substrate, for example a metal surface of a battery, by a coating can be significantly improved when a PVOH and a PAA are blended together, relative to a comparative coating including PVOH as a sole resin or PAA as a sole resin, wherein the sole resin was provided in an amount equal to that of the total PVOH and PAA in the blend. In embodiments, a coating including a blend of PVOH and PAA can have an adhesion value of 3 to 5 according to the Adhesion Test, such as 3, 3.5, 4, 4.5, or 5. In embodiments, a coating having a blend of PVOH and PAA can have an adhesion value of more than 3 and up to 5, according to the Adhesion Test, such as 3.5, 4, 4.5, or 5.

In embodiments, in addition to the water-soluble resin mixture of the disclosure, the coating composition can further include, optionally, one or more additional agents such as aversive agents, antifoaming agents, colorants, and/or plasticizers, e.g. an aversive agent and plasticizer, or an aversive agent, colorant, and plasticizer, etc. An aversive agent such as a bitterant or a pungent can be added as a deterrent to ingestion of the coating composition (and thereby a deterrent to ingestion of a substrate coated with the coating composition), e.g. by a child or animal. A colorant can advantageously act as (1) an indicator of the location of the coating composition, such as the mouth of a child, and thereby indicate the location of the substrate coated with the coating composition, (2) an indicator of ingestion of the coating composition, such as the colorant being present in the stool of a child, and thereby indicate ingestion of the substrate coated with the coating composition, or a combination thereof. The colorant can also act as an indicator of coating quality, e.g. uniformity or positional registry, onto a surface of a substrate.

The coating compositions described herein can include one or more polyvinyl alcohol (PVOH) homopolymers, one or more polyvinyl alcohol copolymers, or a combination thereof. As used herein, the term "homopolymer" generally includes polymers having a single type of monomeric repeating unit (e.g., a polymeric chain consisting of or consisting essentially of a single monomeric repeating unit). For the particular case of PVOH, the term "homopolymer" (or "PVOH homopolymer") further includes copolymers consisting of a distribution of vinyl alcohol monomer units and vinyl acetate monomer units, depending on the degree of hydrolysis (e.g., a polymeric chain consisting of or consisting essentially of vinyl alcohol and vinyl acetate monomer units). In the limiting case of 100% hydrolysis, a PVOH homopolymer can include a true homopolymer having only vinyl alcohol units.

Polyvinyl alcohol is a synthetic resin generally prepared by the alcoholysis, usually termed hydrolysis or saponification, of polyvinyl acetate. Fully hydrolyzed PVOH, where virtually all the acetate groups have been converted to alcohol groups, is a strongly hydrogen-bonded, highly crystalline polymer which dissolves only in hot water—greater than about 140° F. (about 60° C.). If a sufficient number of acetate groups are allowed to remain after the hydrolysis of polyvinyl acetate, that is the PVOH homopolymer is partially hydrolyzed, then the polymer is more weakly hydrogen-bonded, less crystalline, and is generally soluble in cold water—less than about 50° F. (about 10° C.). As such, the partially hydrolyzed polymer is a vinyl alcohol-vinyl acetate copolymer, but is commonly referred to as PVOH homopolymer.

The viscosity of a PVOH homopolymer or copolymer ($\mu$) is determined by measuring a freshly made PVOH solution using Hoeppler falling-ball viscometry, as described in DIN 53015 test method. It is international practice to state the viscosity of 4% aqueous polyvinyl alcohol solutions at 20° C. All viscosities specified in the disclosure in Centipoise (cP) should be understood to refer to the viscosity of 4% aqueous polyvinyl alcohol solution at 20° C., unless specified otherwise. Similarly, when a resin is described as having (or not having) a particular viscosity, unless specified otherwise, it is intended that the specified viscosity is the average viscosity for the resin, which inherently can have a corresponding molecular weight distribution.

It is well known in the art that the viscosity of PVOH resins is correlated with the weight average molecular weight ($\overline{M}w$) of the PVOH resin, and often the viscosity is used as a proxy for the weight average molecular weight. In embodiments, the PVOH resin may have a viscosity of about 1.0 to about 50.0 cP, about 1.0 to about 40.0 cP, or about 1.0 to about 30.0 cP, for example about 4 cP, 8 cP, 15 cP, 17.5, 18 cP, or 23 cP. In embodiments, the PVOH homopolymers or copolymers may have a viscosity of about 1.0 to about 25.0 cP for example, about 1 cP, 1.5 cP, 2 cP, 2.5 cP, 3 cP, 3.5 cP, 4 cP, 4.5 cP, 5 cP, 5.5 cP, 6 cP, 6.5 cP, 7 cP, 7.5 cP, 8 cP, 8.5 cP, 9 cP, 9.5 cP, 10 cP, 11 cP, 12 cP, 13 cP, 14 cP, 15 cP, 17.5 cP, 18 cP, 19 cP, 20 cP, 21 cP, 22 cP, 23 cP, 24 cP, or 25 cP.

In embodiments, the PVOH resin of the coating compositions can have a degree of hydrolysis (D.H. or DH) of at least about 70%, 80%, 84% or 85% and at most about 99.9%, for example in a range of about 70% to about 99.9%, about 75% to about 95%, about 85% to about 88%, about 88% to about 90%, about 84% to about 89%, about 85% to about 99.7%, about 85% to about 95%, about 87% to about 98%, about 89% to about 99%, or about 90% to about 99%, for example about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In embodiments, the degree of hydrolysis of the PVOH is about 88%. As used herein, the degree of hydrolysis is expressed as a mole percentage of vinyl acetate units converted to vinyl alcohol units. When a PVOH resin is described as having (or not having) a particular DH, unless specified otherwise, it is intended that the specified DH is the average DH for the PVOH resin. Specific non-limiting examples of commercially available PVOH resins, corresponding viscosities and degree of hydrolysis include:

| POVAL Grade name | Viscosity [cP] | Degree of hydrolysis [mol %] |
| --- | --- | --- |
| 4-88 | 3.5-4.5 | 86.7-88.7 |
| 6-88 | 5.0-6.0 | 86.7-88.7 |
| 8-88 | 7.0-9.0 | 86.7-88.7 |
| 13-88 | 11.5-14.5 | 86.7-88.7 |
| 18-88 | 16.5-19.8 | 86.7-88.7 |
| 23-88 | 21.5-24.5 | 86.7-88.7 |
| 26-88 | 24.5-27.5 | 86.7-88.7 |
| 32-88 | 30.0-34.0 | 86.7-88.7 |
| 40-88 | 38.0-42.0 | 86.7-88.7 |
| 3-80 | 2.8-3.3 | 78.5-81.5 |
| 26-80 | 21.0-31.0 | 78.0-81.0 |
| 32-80 | 29.0-35.0 | 78.0-81.0 |
| 40-80 | 37.0-45.0 | 78.0-81.0 |
| 5-82 | 4.5-5.2 | 80.0-83.0 |
| 3-85 | 3.4-4.0 | 84.2-86.2 |

The water-soluble resin mixture can comprise one or more different PVOH homopolymers and/or PVOH copolymers. The PVOH homopolymers and/or PVOH copolymers may differ in viscosity, in the degree of hydrolysis, or both, for example.

In embodiments, the water-soluble resin mixture can include a polyvinyl alcohol resin selected from the group consisting of a polyvinyl alcohol homopolymer, a polyvinyl alcohol copolymer having an anionic modification, and combinations of the foregoing. The water-soluble resin mixture can include a PVOH copolymer which can be a PVOH terpolymer including vinyl alcohol monomer units, vinyl acetate monomer units (i.e., when not completely hydrolyzed), and a single type of anionic monomer unit (e.g., where a single type of monomer unit can include equivalent acid forms, salt forms, and optionally ester forms of the anionic monomer unit). In some aspects, the PVOH copolymer can include two or more types of anionic monomer units. General classes of anionic monomer units which can be used for the PVOH copolymer include the vinyl polymerization units corresponding to monocarboxylic acid vinyl monomers, the esters and anhydrides thereof, dicarboxylic monomers having a polymerizable double bond, the esters and anhydrides thereof, and alkali metal salts of any of the foregoing. Examples of suitable anionic monomer units include the vinyl polymerization units resulting from vinyl anionic monomers including but not limited to vinyl acetic acid, maleic acid, monoalkyl maleate, dialkyl maleate, maleic anhydride, fumaric acid, monoalkyl fumarate, dialkyl fumarate, itaconic acid, monoalkyl itaconate, dialkyl itaconate, itaconic anhydride, citraconic acid, monoalkyl citraconate, dialkyl citraconate, citraconic anhydride, mesaconic acid, monoalkyl mesaconate, dialkyl mesaconate, glutaconic acid, monoalkyl glutaconate, dialkyl glutaconate, glutaconic anhydride, alkyl acrylates, alkyl alkacrylates, (methyl)acrylate, vinyl sulfonic acids, alkali metal salts of the foregoing, esters of the foregoing, and combinations of the foregoing.

In embodiments, the anionic monomer unit can be selected from the group consisting of vinyl acetic acid, alkyl acrylates, maleic acid, monoalkyl maleate, dialkyl maleate, monomethyl maleate, dimethyl maleate, maleic anhydride, fumaric acid, monoalkyl fumarate, dialkyl fumarate, monomethyl fumarate, dimethyl fumarate, fitaconic acid, monomethyl itaconate, dimethyl itaconate, itaconic anhydride, citraconic acid, monoalkyl citraconate, dialkyl citraconate, citraconic anhydride, mesaconic acid, monoalkyl mesaconate, dialkyl mesaconate, glutaconic acid, monoalkyl glutaconate, dialkyl glutaconate, glutaconic anhydride, vinyl sulfonic acid, alkyl sulfonic acid, ethylene sulfonic acid, 2-acrylamido-1-methyl propane sulfonic acid, 2-acrylamide-2-methylpropanesulfonic acid, 2-methylacrylamido-2-methylpropanesulfonic acid, 2-sulfoethyl acrylate, alkali metal salts of the foregoing, esters of the foregoing, and combinations of the foregoing.

When the water-soluble resin mixture comprises a PVOH copolymer including an anionic monomer, the level of incorporation of the one or more anionic monomer units in the PVOH copolymer is not particularly limited. In embodiments, the one or more anionic monomer units are present in the PVOH copolymer in an amount in a range of about 1 mol. % to about 10 mol. %, about 1.5 mol. % to about 8 mol. %, about 2 mol. % to about 6 mol. %, about 3 mol. % to about 5 mol. %, or about 1 mol. % to about 4 mol. % (e.g., at least about 1.0, 1.5, 2.0, 2.5, 3.0, 3.5, or 4.0 mol. % and up to about 3.0, 4.0, 4.5, 5.0, 6.0, 8.0, or 10 mol. % in various embodiments).

Without intending to be bound by theory, it is believed that in general, as the molecular weight of the PVOH resin component of the water-soluble resin mixture decreases, the water-soluble resin mixture solubility increases. Increased solubility can correlate to more colorant transfer to a location, such as soft tissue, when colorant is included in the coating composition of the water-soluble resin mixture. The more colorant transferred to a location, specifically soft tissue, the better the indication of contact, prolonged contact, or ingestion. Increased solubility can also correlate to more aversive agent release, thereby increasing the chance of aversive agent contacting a location, such as taste buds and increasing the likelihood that a person, for example a child, will expel the surface or related article before ingestion.

In general, adhesion to glass, silicone rubber, polyester, polyethylene terephthalate (PET), biaxially-oriented polyethylene terephthalate (BoPET), and polished metal surfaces of substrates, such as nickel coated stainless steel batteries as shown below, is generally poor for all PVOH resins, when PVOH is provided as the sole resin, as determined by the Adhesion Test. However, adhesion to unpolished or texturized stainless steel surfaces of substrates is generally acceptable, as determined by the Adhesion Test.

The coating composition described herein can include one or more polyacrylic acids as the PAA resin component of the coating composition.

Polyacrylic acid is a synthetic resin generally prepared by the free radical polymerization of acrylic acid. In the present disclosure, polyacrylic acid can be a homopolymer or copolymer. Polyacrylic acid homopolymers can contain a mixture of acrylic acid monomer units in acid and/or salt form. At low pH, polyacrylic acid exists as a carboxylic acid, however at neutral pH, polyacrylic acid exists almost entirely as an anionic polymer. Thus, depending on the pH of the coating composition, a polyacrylic acid homopolymer component can include polyacrylic acid, polyacrylic acid salt (anionic), or a combination thereof. In embodiments, the water-soluble resin mixture comprises a polyacrylic acid homopolymer. In embodiments, the water-soluble resin mixture can comprise a polyacrylic acid as a homopolymer, a polyacrylic acid copolymer, or a combination thereof.

In embodiments, the polyacrylic acid can have a weight average molecular weight ($\overline{M}w$) of less than about 300,000 Da. In various embodiments, the PAA can have a $\overline{M}w$ in a range of about 1,000 Da to about 300,000 Da. In some embodiments, the PAA can have a $\overline{M}w$ in a range of about 2,000 Da to about 250,000 Da. In embodiments, the PAA can have a $\overline{M}w$ of about 2,000 Da. In embodiments, the PAA can have a $\overline{M}w$ of about 100,000 Da. In embodiments, the PAA can have a $\overline{M}w$ of about 250,000 Da. In various embodiments, the PAA can have a $\overline{M}w$ in a range of about 1,000 Da to about 300,000 Da, such as about 1000 Da, 1500 Da, 2000 Da, 3000 Da, 4000 Da, 5000 Da, 6000 Da, 7000 Da, 8000 Da, 9000 Da, 10,000 Da, 20,000 Da, 30,000 Da, 40,000 Da, 50,000 Da, 100,000 Da, 150,000 Da, 200,000 Da, 240,000 Da, 250,000 Da, 260,000 Da, 270,000 Da, 280,000 Da, 290,000 Da, or 300,000 Da. The weight average molecular weight can be determined by those skilled in the art, for example by methods such as size exclusion chromatography or gel permeation chromatography. When a PAA resin is described as having (or not having) a particular molecular weight, unless specified otherwise, it is intended that the specified molecular weight is the average molecular weight for the resin, which inherently has a corresponding molecular weight distribution.

The molecular weight of the PAA can be selected to provide one or more advantages. For example, without intending to be bound by theory, it is believed that as the molecular weight of the PAA decreases so does the yield point of the coating composition and, as a result, the stringiness and/or the amount of coating composition that shears apart during application decreases, allowing for better coating application control, applications of specific patterns, controlled addition to the top and bottom surfaces of substrates, such as a battery, without affecting the substrate properties, for example, the diameter of a battery or the electrical conductivity of a battery at the anode and cathode, or a combination thereof. However, as demonstrated in the examples herein, adhesion to metal surfaces of substrates such as batteries, is generally poor for all PAA resins when PAA is provided as the sole resin, as determined by the Adhesion Test. Further, as illustrated in the examples below, the adhesion of a PAA-containing coating composition to a metal surface of a substrate generally decreases as the molecular weight of the PAA decreases. The term "yield point" used herein refers to the amount of stress that must be exceeded in order to make the coating composition flow (the coating composition no longer acts elastically).

When the polyacrylic acid resin comprises a copolymer, the acrylic acid can be copolymerized with other monomers, which are typically carboxyl group-containing ethylenically unsaturated monomers, e.g., methyl (meth)acrylate, ethyl (meth)acrylate, n-propyl (meth)acrylate, isopropyl (meth)acrylate, n-butyl (meth)acrylate, isobutyl (meth)acrylate, tert-butyl (meth)acrylate, 2-ethylhexyl acrylate, n-octyl (meth)acrylate, lauryl (meth)acrylate, tridecyl (meth)acrylate, octadecyl (meth)acrylate, isostearyl (meth)acrylate, $C_{1-24}$ alkyl (meth)acrylate, 2-hydroxyethyl (meth)acrylate, hydroxypropyl (meth)acrylate, 2,3-dihydroxy-butyl (meth)acrylate, 4-hydroxybutyl (meth)acrylates such as, polyethylene glycol mono(meth)acrylate, polyhydric monoesters of alcohols with acrylic acid or methacrylic acid hydroxyl group-containing monomers, such as, compounds of ε-caprolactone monoester of alcohol and acrylic acid or methacrylic acid and ring-opening polymerization; styrene, acrylonitrile, methacrylonitrile, and vinyl acetate. In the present disclosure, "(meth)acrylate" encompasses both acrylate and methacrylate.

The water-soluble resin mixture can include one or more water-soluble polymers in addition to the polyvinyl alcohol and the polyacrylic acid. The additional water-soluble polymer can include, but is not limited to, water-soluble acrylate copolymers, polyvinyl pyrrolidone, polyethyleneimine, pullulan, water-soluble natural polymers including, but not limited to, guar gum, gum Acacia, xanthan gum, carrageenan, and starch, water-soluble polymer modified starches, copolymers of the foregoing or a combination of any of the foregoing. Yet other water-soluble polymers can include polyalkylene oxides, polyacrylamides, celluloses, cellulose ethers, cellulose esters, cellulose amides, polyvinyl acetates, polycarboxylic acids and salts thereof, polyaminoacids, polyamides, gelatines, methylcelluloses, carboxymethylcelluloses and salts thereof, dextrins, ethylcelluloses, hydroxyethyl celluloses, hydroxypropyl methylcelluloses, maltodextrins, polymethacrylates, or a combination of any of the foregoing. Such water-soluble polymers are commercially available from a variety of sources. In one type of embodiment, the type and/or amount of additional polymer(s) will not result in the coating having low adhesion to surfaces of substrates, e.g. metal surfaces, or nickel coated substrates.

The coating composition can further include a solvent. In embodiments, the solvent can comprise water. The amount of water provided in the coating composition can be any amount sufficient to solubilize the coating composition. As the amount of water used to solubilize the coating composition decreases, the viscosity of the coating composition generally increases, which can make application of the coating composition to a substrate more difficult, depending on the application method used. Further, as the viscosity of the coating compositions increases, the yield point of the coating composition increases and generally, the amount of shearing apart of the blend, i.e., stringiness, during application also increases. As the stringiness increases, the difficulty of applying a homogenous coating of the blend increases.

Decreased stringiness allows for increased application control, controlled application of specific patterns, controlled addition to the top and bottom surfaces of a substrate such as, a battery, without affecting, for example, the diameter of a battery or the electrical conductivity of a battery at the anode and cathode, or a combination thereof. However, as the amount of water used to solubilize the coating compositions is increased to decrease the viscosity of the coating composition, more time will be needed to dry the coating compositions. In some embodiments, the amount of water present in the coating composition can be 40 wt % or more, based on the total weight of the coating composition. In some embodiments, the amount of water present in the coating composition can be 50 wt % or more, such as 50 wt %, 60 wt %, 70 wt %, 75 wt %, 80 wt %, or 90 wt %, based on the total weight of the coating composition. In embodiments, the amount of water present in the coating composition can be in a range of 40 wt % to 90 wt %, such as in a range of 50 wt % to 90 wt %, 50 wt % to 85 wt %, 50 wt % to 75 wt %, 50 wt % to 60 wt %, 60 wt % to 90 wt %, 60 wt % to 80 wt %, 60 wt % to 75 wt %, or 70 wt % to 90 wt %, based on the total weight of the coating composition.

In embodiments, the solvent can comprise any suitable solvent or solvent blend that is sufficient to solubilize the coating composition. In embodiments, the solvent can comprise lower alcohols such as methanol, ethanol, isopropanol, or butanol. A lower alcohol, such as methanol or ethanol, when included in the solvent, can reduce the amount of drying time needed for the coating composition compared to a coating composition using water as the lone solvent.

In embodiments, the coating composition described herein can further comprise isopropanol as a solvent or part of a solvent blend. The isopropanol can be used to reduce the viscosity of the coating composition and/or improve blocking of PAA and reduce cross-linking between PVOH and PAA during storage. Without intending to be bound by theory, it is believed that crosslinking can occur by nucleophilic attack of a carboxylate anion of the PAA on the alpha-carbon of a protonated hydroxyl of the PVOH (i.e. R—OH$_2^+$), thereby replacing a hydroxyl of the PVOH with an ester linkage to the PAA and providing a poly(vinyl acetate-co-alcohol-co-acrylic acid) network formation. In some embodiments, crosslinking can occur at high temperatures.

In embodiments, the coating composition can comprise any suitable plasticizer. A plasticizer is a liquid, solid, or semi-solid that is added to a material (usually a resin or elastomer) making that material softer, more flexible (by decreasing the glass-transition temperature of the polymer), or easier to process. In addition or in alternative, a polymer can be internally plasticized by chemically modifying the polymer or monomer. In embodiments, the coating composition described herein can comprise one or more plasticizers. In embodiments, the plasticizer can comprise glycerol, diglycerin, sorbitol, ethylene glycol, diethylene glycol, triethylene glycol, dipropylene glycol, tetraethylene glycol, propylene glycol, polyethylene glycols up to 400 Da molecular weight, hexylene glycol, neopentyl glycol, trimethylolpropane, polyether polyols, polyether diol, polyether triol, xylitol, 2-methyl-1,3-propanediol (MPDiol®), ethanolamines, glycerol propylene oxide polymers (such as, for example, Voranol™ available from The Dow Chemical Company), or a mixture thereof.

When the coating composition includes a plasticizer, the plasticizer can be provided in a range of about 1 wt. % to about 45 wt. %, or about 5 wt. % to about 35 wt. %, or about 10 wt. % to about 30 wt. %, or about 15 wt. % to about 45 wt. %, for example about 1 wt. %, 5 wt. %, 10 wt. %, 15 wt. %, 20 wt. %, or 25 wt. %, based on the total weight of the coating composition weight. Without intending to be bound by theory, it is believed that at low plasticizer levels, coatings may become brittle or prone to breaking and at elevated plasticizer levels, coatings may be too soft or weak for a desired use.

The aversive agent of the present disclosure can include bitterants, pungents, or any other suitable aversive compound, e.g. acrid agents and astringent agents. In embodiments, the aversive agent can be selected from bitterants and pungents. In embodiments, the aversive agent can be one or more bitterants. All chemical compounds which have a bitter taste are designated as bitterants herein. In embodiments, the aversive agent disclosed herein can comprise a bitterant with a bitterness value of at least 10,000. In embodiments, the aversive agent can comprise a bitterant with a bitterness value of at least 100,000. The standardized method described in the European Pharmacopoeia (5th Edition, Main Volume, Stuttgart 2005, Volume 1, General Part, Monograph Groups, 2.8.15 Bitterness Value, p. 278) is used to determine the bitterness value.

In embodiments, suitable bitterants can include, but are not limited to, denatonium salts (including, but not limited to, denatonium benzoate, denatonium saccharide, denatonium chloride), sucrose octaacetate (bitterness value=100,000), quinine, flavonoids (including, but not limited to, quercetin, naringen (bitterness value=10,000), glycosides, isoprenoids, alkaloids, amino acids, and quassinoids (including, but not limited to, quassin, brucine). In embodiments, the aversive agent comprises a denatonium salt comprising denatonium benzoate, denatonium saccharide, denatonium chloride, or a combination thereof. In embodiments, the aversive agent comprises denatonium benzoate (bitterness value>100,000,000). A pungent generally has a sharp biting taste when ingested and a burning sensation when topically applied to skin. Suitable pungents include, but are not limited to, capsaicin, piperine, allyl isothiocyanate, and resinferatoxin. The aversive agents can be added in an amount sufficient to cause an aversive response such as bitterness, when the coating composition or a coating formed therefrom comes in contact with taste buds or a burning sensation when the coating composition or a coating formed therefrom comes in contact with soft tissue such as lips, cheeks, tongue, or skin. Suitable levels of incorporation vary according to the particular bitterant or pungent material. The aversive component should be incorporated at a level sufficient to impart the unpleasant taste or sensation, while avoiding levels that can lead to potential toxicity from the aversive agent itself.

The aversive agent in the present disclosure can be diluted from a commercially-supplied form or otherwise mixed with a solvent for ease in mixing with other components of the coating composition or added in a dry powder or crystalline form. Suitable solvents for diluting an aversive agent may be selected from water, lower molecular weight alcohols (such as methanol, ethanol, propanol, or butanol) or one or more of the plasticizers disclosed herein.

In embodiments, the aversive agent can be diluted in any suitable water-soluble plasticizer. In embodiments, the aversive agent can be diluted in propylene glycol. In embodiments, the aversive agent can be provided in a solution of propylene glycol in an amount in a range of 1 wt % to 50 wt % based on the weight of the total solution, for example 5 wt %, 10 wt %, 15 wt %, 20 wt %, 25 wt %, 30 wt %, 35 wt %, 40 wt %, 45 wt %, based on the weight of the total solution. In embodiments, the aversive agent can be provided in a solution of propylene glycol in an amount of 25 wt %, based on the weight of the total solution.

In embodiments, the amount of aversive agent in the coating composition is 1000 ppm or more of the total dry weight of the coating composition. In embodiments, the amount of aversive agent in the coating composition is 30,000 ppm or less of the total weight of the coating composition. In embodiments, the amount of aversive agent in the coating composition is in a range of 1000 ppm to 30,000 ppm of the total weight of the coating composition, for example, 1000 ppm, 2000 ppm, 3000 ppm, 4000 ppm, 5000 ppm, 6000 ppm, 7000 ppm, 8000 ppm, 9000 ppm, 10,000 ppm, 11,000 ppm, 12,000 ppm, 13,000 ppm, 14,000 ppm, 15,000 ppm, 16,000 ppm, 17,000 ppm, 18,000 ppm, 19,000 ppm, 20,000 ppm, 25,000 ppm, or 30,000 ppm.

In embodiments, the coating composition described herein can comprise a colorant. In embodiments, the coating composition can comprise a colorant and water. Suitable colorants can include food colorants. In embodiments, the colorant comprises a dye. In embodiments, the colorant comprises a water-soluble dye. In embodiments, the colorant comprises an indicator dye, such as a pH indicator (e.g., thymol blue, bromothymol, thymolphthalein, and thymolphthalein), or a moisture/water indicator (e.g., hydrochromic inks or leuco dyes). In embodiments, the indicator dye is clear when dry but colored when it is wet. In embodiments, the colorant comprises a thermochromic ink, wherein the ink changes color when temperature increases and/or decreases. In embodiments, the colorant comprises a hydrochromic ink, wherein the ink changes color when in contact with water. In embodiments, the colorant comprises a triphenylmethane dye, an azo dye, an anthraquinone dye, a perylene dye, an indigoid dye, a food, drug and cosmetic (FD&C) colorant, an organic pigment, an inorganic pigment, or a combination thereof. In embodiments, the coating composition comprises a FD&C colorant. In some embodiments, the colorants are selected from the group consisting of: FD&C Red #40; Red #3; FD&C Black #3; Black #2; Mica-based pearlescent pigment; FD&C Yellow #6; Green #3; Blue #1; Blue #2; titanium dioxide (food grade); brilliant black; and a combination thereof. In embodiments, the colorant comprises more than one FD&C colorant and is black in color.

In embodiments, the coating composition comprises a colorant, wherein the colorant is at a concentration±30% of the saturation point of the colorant. In embodiments, the colorant can be at a concentration±10% of the saturation point of the colorant. The colorant can be at a concentration within at least ±10%, at least ±7.5%, at least ±5%, or at least ±2.5% of the saturation point. The term "saturation point" herein refers to the point at which no more colorant can be dissolved into a solution of the PVOH, PAA and water. When the resulting solution is dried, the solution can form a continuous homogenous layer.

In embodiments, the colorant is present in the coating compositions in an amount of at least 1 part colorant to 70 parts water, for example, in a range of 1 part to 30 parts colorant to 70 parts water. In embodiments, the colorant is present in the coating composition in an amount of at least 10 parts colorant to 70 parts water, such as 11 parts colorant to 70 parts water, 12 parts colorant to 70 parts water, 13 parts colorant to 70 parts water, 14 parts colorant to 70 parts water, 15 parts colorant to 70 parts water, 16 parts colorant to 70 parts water, 17 parts colorant to 70 parts water, 18 parts colorant to 70 parts water, 19 parts colorant to 70 parts water, 20 parts colorant to 70 parts water, 21 parts colorant to 70 parts water, 22 parts colorant to 70 parts water, 23 parts colorant to 70 parts water, 24 parts colorant to 70 parts water, 25 parts colorant to 70 parts water, 26 parts colorant to 70 parts water, 27 parts colorant to 70 parts water, 28 parts colorant to 70 parts water, 29 parts colorant to 70 parts water, or 30 parts colorant to 70 parts water.

In embodiments, the colorant can be provided in an amount of 5% to 25% by weight of the water-soluble resin mixture. In embodiments, the colorant can be provided in an amount of 5% to 25% by weight of the water-soluble resin mixture, such as, 6%, 7%, 8%, 9%, 10%, 11%, 12%, 13%, 14%, 15%, 16%, 17%, 18%, 19%, 20%, 21%, 22%, 23%, and 24%, by weight of the water-soluble resin mixture. In embodiments, the colorant can be provided in an amount of about 10% to 18% by weight of the water-soluble resin mixture, for example, about 11% to 17%, 12% to 16%, 13% to 16%, 13% to 15%, or about 15%, by weight of the water-soluble resin mixture. Without intending to be bound by theory, it is believed that when the colorant content of the coating composition is increased above about 25% by weight of the water-soluble resin mixture, the benefit of increased color intensity is only marginal compared to that of a coating having colorant in an amount of about 25% by weight of the water-soluble resin mixture and the colorant is too easily transferred to an undesirable substrate, for example, secondary packaging. Further without intending to be bound by theory, it is believed that a coating composition having a colorant content less than about 5% by weight of the water-soluble resin mixture will have good adhesion according to the adhesion test but will not be concentrated enough to transfer enough colorant to be easily seen by the human eye on soft tissue and thus has decreased functionality as an indicator. In embodiments, the colorant makes up at least 10% and up to 99% by weight of the solids content of the coating composition, for example, at least 10%, at least 12%, at least 15%, at least 17%, at least 20%, at least 25%, at least 30%, at least 40%, or at least 50% by weight of the solids content of the mixture, and up to 99%, up to 95%, up to 93%, up to 90%, up to 80%, up to 70%, up to 60%, up to 50%, up to 40%, or up to 30%. In embodiments, the colorant can be bound to a starch and/or a modified starch. The term "bound to a starch" refers to being encapsulated and/or covalently bonded to starch. Without intending to be bound by theory, it is believed that because starch is sensitive to saliva and/or other activation solvents, in the presence of such solvents or saliva, the starch will breakdown or dissolve, thereby releasing the colorant. When the colorant is released, the solution or location is turned the color of the colorant. The coating composition, thereby, advantageously has child safety features, for example rapid transfer of high colorant content to a soft tissue environment such as, lips, cheeks, or tongue in part due to the breakdown of starch in the presence of saliva or activation solvents, and deterring ingestion of a surface of a substrate. However, many starches are insoluble in water, so, when the colorant is bound to a water-insoluble starch, the coating composition containing the colorant bound to a water-insoluble starch, can be resistant to easy colorant transfer to wet or moist hands. The colorant bound to a water-insoluble starch, thereby encapsulated by starch particles reducing its mobility, is resistant to easy colorant transfer to wet or moist hands. Non-limiting examples of modified starches include ethylated starch, hydroxyethylated starch, propylated starch, hydroxypropylated starch, and acetate modified starch. In embodiments, two or more starches can be used together to form a starch blend. Starch blends can include combinations such as two unmodified starches, two modified starches, or an unmodified starch and a modified starch.

The one or more starches can be provided in a total amount of at least about 5 phr, 6 phr, 7 phr, 10 phr, 12 phr, 15 phr, 20 phr, 22 phr, 25 phr, 30 phr, 35 phr, 40 phr, 45 phr, 50 phr, and up to about 5 phr, 10 phr, 12 phr, 16 phr, 20 phr, 22 phr, 24 phr, 26 phr, 30 phr, 40 phr, 50 phr, or 60 phr based on the total amount of the coating composition. For example, the starch can be provided in an amount in a range of about 2.5 phr to about 30 phr, or about 5 phr to about 60 phr, or about 5 phr to about 400 phr, or about 5 phr to about 30 phr, or about 6 phr to about 25 phr, or about 12 phr to about 20 phr, or about 2 phr, about 2.5 phr, about 3 phr, about 7 phr, about 8 phr, about 9 phr, about 13 phr, about 14 phr, about 16 phr, about 20 phr, about 22 phr, about 24 phr, about 25 phr, or about 30 phr.

In embodiments, the coating composition can be substantially colorant free. As used herein, the term "substantially colorant free" refers to the colorant being present in the coating composition in an amount less than about 500 ppm. For example, less than about 400 ppm, less than about 300 ppm, less than about 200 ppm, less than about 100 ppm, less than about 75 ppm, less than about 50 ppm, or less than about 25 ppm.

The coating composition herein can comprise an anti-foaming agent and/or a surfactant. Anti-foaming agents can aid in coalescing of foam bubbles, thereby reducing the amount of foaming in the coating composition. Suitable anti-foaming agents for use in coating compositions according to the present disclosure include, but are not limited to, hydrophobic silicas, for example silicon dioxide or fumed silica in fine particle sizes, and Foam Blast® anti-foaming agents available from Emerald Performance Materials, including Foam Blast® 327, Foam Blast® UVD, Foam Blast® 163, Foam Blast® 269, Foam Blast® 338, Foam Blast® 290, Foam Blast® 332, Foam Blast® 349, Foam Blast® 550 and Foam Blast® 339, which are proprietary, non-mineral oil anti-foaming agents. In embodiments, anti-foaming agents can be used in an amount in a range of about 0.1 phr (parts per one hundred parts PVOH) to about 1 phr, for example, about 0.1 phr, about 0.2 phr, about 0.3 phr, about 0.4 phr, about 0.5 phr, about 0.6 phr, about 0.7 phr, about 0.8 phr, about 0.9 phr, or about 1 phr. In embodiments, anti-foaming agents can be used in an amount in a range of about 0.6 phr to about 0.8 phr. In embodiments, anti-foaming agents can be used in an amount of about 0.7 parts per one hundred parts PVOH.

In embodiments, the coating composition can comprise any suitable surfactant. Optionally, surfactants are included to aid in the dispersion of the coating composition. Suitable surfactants for use in the coating composition provided herein can include nonionic, cationic, anionic, and zwitterionic classes. Suitable surfactants include, but are not limited to, propylene glycols, diethylene glycols, monoethanolamine, polyoxyethylenated polyoxypropylene glycols, alcohol ethoxylates, alkylphenol ethoxylates, tertiary acetylenic glycols and alkanolamides (nonionics), monoacetin, triacetin, triethyl citrate, sorbitol, 1, 3-butanediol, D-glucono-1,5-lactone, polyoxyethylenated amines, quaternary ammonium salts and quaternized polyoxyethylenated amines (cationics), alkali metal salts of higher fatty acids containing about 8 to 24 carbon atoms, alkyl sulfates, alkyl polyethoxylate sulfates and alkylbenzene sulfonates (anionics), and amine oxides, N-alkylbetaines and sulfobetaines (zwitterionics). Other suitable surfactants include dialkyl sulfosuccinates, lactylated fatty acid esters of glycerol and propylene glycol, lactylic esters of fatty acids, sodium alkyl sulfates, polysorbate 20, polysorbate 60, polysorbate 65, polysorbate 80, alkyl polyethylene glycol, lecithin, acetylated fatty acid esters of glycerol and propylene glycol, sodium lauryl sulfate, acetylated esters of fatty acids, myristyl dimethylamine oxide, trimethyl tallow alkyl ammonium chloride, quaternary ammonium compounds, salts thereof and combinations of any of the foregoing. In embodiments, the surfactant is selected from the group consisting of a polyoxyethylenated polyoxypropylene glycol, an alcohol ethoxylate, an alkylphenol ethoxylate, a tertiary acetylenic glycol and alkanolamide, a polyoxyethylenated amine, a quaternary ammonium salt and quaternized polyoxyethylenated amine, and an amine oxide, a N-alkylbetaine, a sulfobetaine, and a combination thereof.

In various embodiments, when a surfactant is included in the coating composition, the amount of surfactant in the coating composition is in a range of about 0.1 wt % to about 8.0 wt %, or about 1.0 wt % to about 7.0 wt %, or about 3 wt % to about 7 wt %, or about 5 wt % to about 7 wt %, or about 0.1 wt % to 2.5 wt %, based on the total weight of the coating composition.

In embodiments, a surfactant may be used in the coating composition to enhance adhesion of the coating composition to a surface of a substrate. For example, ionic surfactants such as the zwitterionic, cationic, and anionic surfactants, may increase the affinity of the coating with ionic surfaces of substrates (e.g., metal surfaces), improving overall adhesion of the coating composition. In the same way, non-ionic surfactants may increase the affinity of the coating with non-ionic substrate surfaces (e.g., plastics), improving overall adhesion of the coating composition to the substrate surface.

The coating composition can further comprise other auxiliary agents and processing agents, such as, but not limited to, electrical conductors, plasticizer compatibilizers, lubricants, release agents, fillers, extenders, cross-linking agents, antiblocking agents, detackifying agents, nanoparticles, including layered silicate-type nanoclays (e.g., sodium montmorillonite), bleaching agents (e.g., sodium metabisulfite, sodium bisulfite or others), and other functional ingredients, in amounts suitable for their intended purposes. The coating composition can include a secondary component including, but not limited to, crosslinked polyvinylpyrrolidone, crosslinked cellulose, microcrystalline cellulose, silica, metallic oxides, calcium carbonate, talc, mica, stearic acid and metal salts thereof (e.g., magnesium stearate), or a combination thereof. In embodiments, the amount of secondary components in the coating composition can be in a range of about 0.1 wt. % to about 6 wt. %, or about 1 wt. % to about 5 wt. %, or about 1 wt. % to about 4 wt. %, for example, 0.1 wt. %, 0.5 wt. %, 1 wt. %, 2 wt. %, 3 wt. %, 4 wt. %, or 5 wt. %, based on the total weight of the coating composition.

In embodiments, the coating composition can comprise any suitable electrical conductor known to one of skill in the art that does not affect adhesion to substrates described herein. In embodiments, the coating composition can comprise any suitable electrical conductor, such as metal oxides, metal fiber, conductive inks, carbon and graphite electrical conductive fillers, for example carbon nanotubes.

The coating described herein comprises a first water-soluble layer, the first water-soluble layer comprising a dried first coating composition comprising a PVOH and a PAA. The term "water-soluble layer" herein refers to a layer that has a percent dissolution of 8 or more according to the Dissolution Test, described below. The dried first coating composition of the coating can include any embodiment of the coating compositions described above or in the Examples below that is dried, for example, a water-soluble resin mixture comprising a PVOH, a polyacrylic acid (PAA) and a colorant, wherein the colorant is at a concentration±10% of the saturation point of the colorant before it is dried. The term "dried first coating composition" or "dried second coating composition" herein refers to a coating composition described above or in the Examples below, wherein more than 85% of the water has been removed, for example more than 86%, more than 88%, more than 90%, more than 92%, more than 94%, or more than 96% of the water has been removed. The terms "dried first coating composition" or "dried second coating composition" herein can also be characterized by the residual moisture content, wherein the dried coating compositions herein have less than 15%, less than 14%, less than 12%, less than 10%, less than 8%, less than 6%, less than 4%, less than 2%, or less than 1% residual water content, as measured by Karl Fischer titration. In embodiments, when first coating composition is dried, the first coating composition no longer has a colorant at a concentration±10% of the saturation point of the colorant, as the coating composition is no longer a solution, instead it is a continuous homogenous layer and does not have a colorant saturation point. In embodiments, the coating herein further comprises a second water-soluble layer, the second water-soluble layer comprising a dried second coating composition.

The coating described herein can be selected based on average percent dissolution values and average values of adhesion to a substrate surface, according to the Dissolution Test and Adhesion Test described herein. In general, an adhesion value of 3 or more indicates acceptable adhesion to a surface of a substrate, for example a metal surface. Described herein, a higher dissolution percentage corresponds to an advantageous faster transfer/release of colorant from the coatings of the disclosure, aversive agent from the coatings of the disclosure, or a combination thereof, when contacted with sufficient moisture, e.g. in the mouth of a child, relative to a coating having a lower dissolution percentage. However, if the percent dissolution increases above, e.g., ~50, the coating may be too easily dissolved by atmospheric moisture or, for example, warm and/or moist hands. Thus, in embodiments, the coating has a percent dissolution of 10 or greater, about 13 or greater, about 15 or greater, or about 17 or greater, and up to about 25, up to about 27, up to about 30, up to about 32, up to about 35, up to about 40, up to about 45, or up to about 50. In embodiments, the coating has a percent dissolution of 17 or greater. In embodiments, the coating has a percent dissolution in a range of about 17 to about 50. In embodiments, the coating has a percent dissolution in a range of about 15 to about 35. In embodiments, the coating has a percent dissolution of greater than 17 and less than 32. In embodiments, the coating has an average percent dissolution of about 10 to 35, such as 10, 11, 12, 13, 14, 15, 16, 17, 18, 19, 20, 21, 22, 23, 24, 25, 26, 27, 28, 29, 30, 31, 32, 33, 34, or 35. As demonstrated in the Examples, below, coating compositions including PAA having a $\overline{M}w$ of about 2,000 Da or less as the sole resin exhibit a high dissolution percentage according to the Dissolution Test described below, however said coating composition exhibits poor adhesion with a value of 0. Accordingly, a coating comprising PAA having a $\overline{M}w$ of about 2,000 Da or less as the sole resin is typically considered unsuitable for coating a metal surface of a substrate.

The second coating composition can include any water-soluble resin and optionally one or more additional components selected from aversive agents, colorants, solvents, plasticizers, anti-foaming agents, surfactants or other secondary component disclosed herein. In embodiments, the coating can comprise the second coating composition when the dried first coating composition has a dissolution percentage of 20 or more and up to 100, for example, 21 or more, 22 or more, 23 or more, 24 or more, 25 or more, 26 or more, 27 or more, 28 or more, 29 or more, or 30 or more. In embodiments, the second coating composition can comprise a water-soluble polymer. The water-soluble polymer of the second coating composition can include any water-soluble polymer described herein. In embodiments, the second coating composition can comprise a polyvinyl alcohol as disclosed herein. In embodiments, the water-soluble resin of the second coating composition does not include PAA. In embodiments, the PVOH of the second coating composition can have a viscosity in a 4% aqueous solution at 20° C. in a range of 1 cP to 18 cP, such as, 1 cP to 15 cP, 1 cP to 10 cP, 1 to 8 cP, or 1 to 5 cP, for example, 1 cP, 2 cP, 3 cP, 4 cP, 5 cP, 6 cP, 7 cP, 8 cP, 9 cP, 10 cP, 11 cP, 12 cP, 13 cP, 14 cP, 15 cP, 16 cP, 17 cP, or 18 cP. In embodiments, the PVOH of the second coating composition can have a viscosity in a 4% aqueous solution at 20° C. in a range of 1 cP to 10 cP. In embodiments, the PVOH of the second coating composition can have a degree of hydrolysis in a range of about 75% to about 99%, such as about 75% to about 95%, about 75% to about 90%, about 80% to about 99%, about 80% to about 95%, about 85% to about 99%, about 85% to about 95%, for example, about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. In embodiments, the PVOH of the second coating composition can have a degree of hydrolysis in a range of about 85% to 95%. In embodiments, the PVOH of the second coating composition can have a degree of hydrolysis of about 88%.

In embodiments, the second coating composition can be used to prepare a second water-soluble layer. In embodiments, the second water-soluble layer can be free of a colorant. In embodiments, the second coating composition can be free of a colorant. In embodiments, the second coating composition, and the second water-soluble layer can be free of a colorant. The term "free of a colorant" refers to a water-soluble layer or a coating composition having an amount of colorant of about 50 parts per billion (ppb) or less, about 40 ppb or less, about 30 ppb or less, about 20 ppb or less, about 10 ppb or less, about 5 ppb or less, or about 1 ppb or less.

In embodiments, the second coating composition further comprises a plasticizer. The plasticizer can include any plasticizer disclosed herein. In embodiments, the second coating composition comprises glycerol.

In embodiments, the second coating composition can comprise a plasticizer in a range of 8:1 to 1:1 parts PVOH present in the second coating composition to parts plasticizer, by weight, for example, 8:1, 7:1, 6:1, 5.5:1, 5:1, 4.5:1, 4:1, 3.5:1, 3:1, 2.5:1, 2:1, 1.5:1, 1:1 parts PVOH present in the second coating composition to parts plasticizer. In embodiments, the plasticizer is in a range of 5:1 to 3:1 parts PVOH present in the second coating composition to parts plasticizer, by weight, such as 5:1, 4.5:1, 4:1, 3.5:1, or 3:1. In embodiments, the plasticizer comprises glycerol and is present in the second coating composition in the amount of 4:1 parts PVOH present in the second coating composition to parts plasticizer, by weight.

The thickness of the coating comprising the first layer, the second layer or the first and second layer, is not particularly limiting, and can be selected based on the desired end use. For example, for a battery application, the thickness of the coating may be limited by the amount of available free space in a battery chamber of a device (e.g., the coating cannot make the battery too big to fit in the device). In embodiments, the coating disclosed herein can have a thickness of about 1 mil (25.4 µm) to about 1000 mil (25.4 mm). In embodiments, the coating disclosed herein can have a thickness of about 0.1 mil (2.54 µm) to about 1000 mil (25.4 mm). In embodiments, the coating disclosed herein can have a thickness in a range of about 0.1 mil (2.54 µm) to 20 mil (508 µm), such as about 0.1 mil, 0.2 mil, 0.3 mil, 0.4 mil, 0.5 mil, 0.6 mil, 0.7 mil, 0.8 mil, 0.9 mil, 1 mil, 1.5 mil, 2 mil, 3 mil, 4 mil, 5 mil, 6 mil, 7 mil, 8 mil, 9 mil, 10 mil, 11 mil, 12 mil, 13 mil, 14 mil, 15 mil, 16 mil, 17 mil, 18 mil, 19 mil, or 20 mil. In some embodiments, the coating can have a thickness of no greater than about 2 mil (50.8 µm). In some embodiments, the coating can have a thickness of no greater than about 1 mil (25.4 µm). In general, the thicker the coating is, the more time the coating will take to completely dissolve.

In embodiments, the coating can be provided on a surface of a substrate, for example a metal surface of a battery. In embodiments, the first water-soluble layer is provided on the surface of the substrate and the second layer comprises the outermost layer, e.g., distal to the substrate surface. In embodiments, the second water-soluble layer can be provided on the first water-soluble layer. In embodiments, the first water-soluble layer is provided in contact with the surface of the substrate and the second layer comprises the outermost layer, e.g., distal to the substrate surface. In embodiments, the second water-soluble layer can be provided in contact with the first water-soluble layer. When the second water-soluble layer is the outermost layer, the coating can have fast release/transfer of colorant, as described herein, but also can allow for freedom of formulation of the first water-soluble layer.

In embodiments, the coating composition can be applied to the surface of a substrate, such that the coating composition does not cover the entire surface of the substrate. In embodiments, the coating composition can be applied to the surface of a substrate, such that the coating composition is applied in a particular pattern or design on the surface of the substrate, such as a ring. The coating can be applied in any shape, pattern, or design that does not cover the entire surface of the substrate, such as a ring, concentric circles, a matrix of dots, a grid pattern, or any shape having an opening in the center, such as a triangle, square, or a circle.

In embodiments, the coating is applied to a surface of an electrical conducting metal substrate, such as a coin/button battery, in an amount such that the resistance of the electrical conducting metal substrate is within ±10% of the resistance of the electrical conducting metal substrate, for example within 9%, 8%, 7%, 6%, 5%, 4%, 3%, 2%, 1%, 0.5%, 0.1%, 0.05%, 0.01%, or 0.001%, before the coating or coating composition is applied to the electrical conducting metal substrate. For example, in embodiments, the surface area of the electrical conducting metal substrate covered by the coating composition or coating can be 100%, 90%, 75%, 50%, 25%, or 10% or less. The resistance of an electrical conducting metal surface can be measured using an ohm-meter or multimeter (volt-ohm-milliammeter), as is known in the art. In the particular case of a battery, the change in resistance can also be determined by measuring the change in current of the battery prior to and after applying the coating composition, at constant voltage. The current can be measured using a multimeter, as is known in the art.

In embodiments, the coating composition can be dried before it is applied to the surface of a substrate, such as the metal surface of a battery. In embodiments, the dried coating composition can be transferred to a surface of a substrate. In embodiments, the dried coating composition can be rolled into a coating roll, the dried coating composition on the coating roll can then be transferred to a surface of a substrate, for example a metal surface of a battery. In embodiments, the coating composition can be cast onto a material to which the coating composition does not strongly adhere. The cast coating composition can then be dried and subsequently transferred onto a surface of a substrate described herein. In embodiments, the coating composition can be applied to the surface of a substrate comprising an adhesive layer. The term "adhesive layer" herein refers to a layer adjacent to the surface of the substrate, that is used to adhere the coating composition to the surface of the substrate, the adhesive layer having a larger adhesive value with the coating composition relative to the surface of the substrate, according to the Adhesion Test. In some embodiments, the surface of the substrate and/or dried coating composition can be wetted to improve transferability and/or adhesion of the coating composition to the substrate surface.

In embodiments, the surface of the substrate comprises metal, plastic, wood, glass, paper, composite, ceramic, stone, rubber, or a combination thereof. In embodiments, the surface of the substrate can optionally be magnetic. In embodiments, the surface of the substrate comprises a metal surface. In embodiments, the metal surface of the substrate comprises nickel, steel, aluminum, zinc, copper, tin, iron, an aluminum-zinc alloy, or a combination thereof. In embodiments, the metal surface of the substrate is nickel. In embodiments, the substrate comprises metal, plastics, wood, glass, paper, composites, ceramic, stone, rubber, or a combination thereof. In embodiments, the substrate can optionally be magnetic. In embodiments, the substrate comprises metal. In embodiments, the substrate comprises nickel coated stainless steel, aluminum coated steel, zinc coated steel, copper coated steel, tin coated steel, aluminum-zinc alloy, or a combination thereof. In embodiments, the substrate comprises nickel coated stainless steel. In embodiments, the substrate is electrically-conductive. In embodiments, the substrate may comprise a first surface and a second surface, wherein the first and second surfaces may comprise different materials, such as metal, plastic, wood, glass, paper, composite, ceramic, stone, or rubber. In embodiments, the first and second surfaces can optionally be magnetic. In embodiments, the substrate may comprise a first metal surface and a second metal surface, wherein the first metal surface and the second metal surface comprise different metals, for example, a coin cell battery wherein the anode can be coated with one metal surface and the cathode can be coated with a different metal surface.

Further disclosed herein is a surface of a substrate comprising a coating or coatings described herein. In embodiments, the surface of a substrate can be one or more surfaces of any object that may benefit from having a coating composition of the disclosure provided thereon, for example, a battery, a battery electrode, a coin cell/button cell battery, a children's toy, a hand tool, a medical device or medical device component, an industrial component, or other plastic, glass, paper, metal, ceramic, wood, rubber, stone, or composite objects. In embodiments, the surface of the substrate can optionally be magnetic. In embodiments, the surface of the substrate is metal and the metal surface can be one or more surfaces of any substrate that may benefit from having a coating composition of the disclosure provided thereon, for example, a battery, a battery electrode, a coin cell/button cell battery, a children's toy, a hand tool, a medical device or medical device component, or an industrial component.

In embodiments, the coating described herein can be applied to a surface of a substrate by contacting the surface of the substrate with a coating composition disclosed herein. The surface of a substrate can be any surface disclosed herein. The coating composition described herein can be applied to a surface of a substrate by any suitable method, including known coating methods. In embodiments, applying the coating composition comprises ink jet printing, needle deposition, dip coating, curtain coating, spray coating, pad printing, gravure printing, reverse gravure printing, or a combination thereof. In embodiments, applying the coating composition comprises ink jet printing, needle deposition, or a combination thereof.

As disclosed in the examples, the PVOH films and coatings do not inherently adhere to metal surfaces, such as nickel surfaces. Advantageously, as shown in the Examples herein, when a coating includes a PVOH blended with a PAA, adhesion to metal surfaces, such as nickel, is improved. In embodiments, the coating can have an adhesion value of 3 or greater in accordance with the Adhesion Test (e.g., adhesion value of 3, 3.5, 4, 4.5, or 5).

Further disclosed herein is a method of deterring ingestion of a substrate comprising applying to a surface of the substrate a coating composition disclosed herein. The substrate can be any substrate disclosed herein. In embodiments, the surface of the substrate is metal. In embodiments, the metal surface of the substrate comprises nickel.

In embodiments, the method of deterring ingestion of a substrate can comprise applying a coating composition disclosed herein to a surface of the substrate by ink jet printing, needle deposition, dip coating, curtain coating, spray coating, pad printing, gravure printing, reverse gravure printing, or a combination thereof. In embodiments, the method of deterring ingestion of a substrate can comprise applying a coating composition described herein to a surface of the substrate by ink jet printing, needle deposition, or a combination thereof.

Another aspect of the disclosure herein is a kit comprising a substrate having a surface coated with the dried coating composition described herein and instructions to not wash, rinse, or otherwise contact the substrate surface with water or solvents.

Adhesion Test

Figure 1:
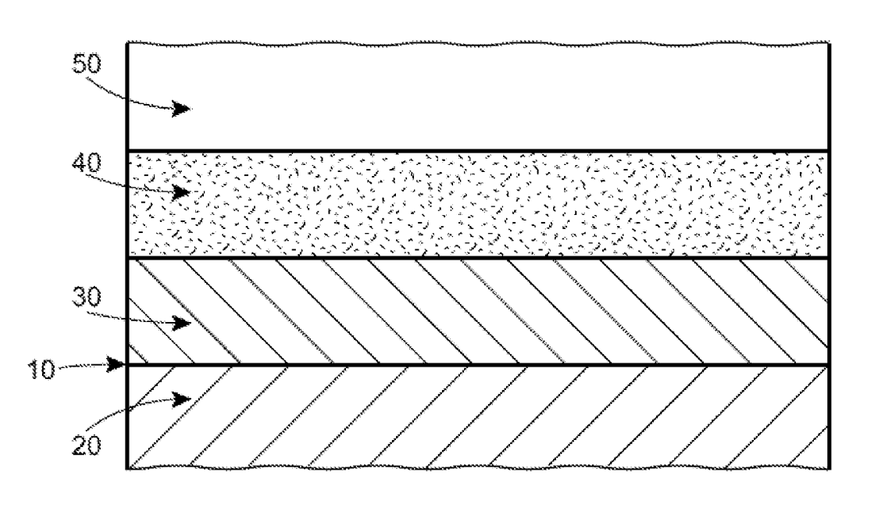
FIG. 1 shows an illustration of an example of a substrate surface (10), a substrate (20), a coating composition (30), an optional second water-soluble layer (40), and the air or surface surrounding the example (50).

The methods used to test the adhesion of the coatings of the disclosure generally follow the procedure of ASTM D3359-09 (2009, Version ε²) Test Method B ("Standard Test Methods for Measuring Adhesion by Tape Test") with slight modifications. The slightly modified ASTM D3359-09 method is detailed below and is referred to herein as the "Adhesion Test." The classification of adhesion value test results on a scale from 0-5 used herein, are described in detail by ASTM D3359-09 Test Method B, FIG. 1. The procedure and reporting methods are described herein:
1. Preparation and Testing of Samples
    1.1. For laboratory use, apply the materials to be tested (i.e., the coating) to a plurality of substrates on which it is desired to determine the adhesion. For example, the samples can be nickel coated stainless steel coin batteries coated with a coating described herein.
    1.2. Samples should be mounted, using either double-sided tape mounted on a self-healing cutting mat, or using a vice clamp if appropriate.
    1.3. The samples should be mounted in such a way that the coated side of the sample is facing up to be easily accessible and allows easy maneuvering with a razor-blade.
    1.4. Select an area free of blemishes and minor surface imperfections. For tests in the field, ensure that the surface is clean and dry. Extremes in temperature or relative humidity may affect the adhesion of the tape or the coating.
    1.5. For specimens which have been immersed: after immersion, clean and wipe the surface with an appropriate solvent which will not harm the integrity of the coating. Then dry or prepare the surface, or both, as requested.
    1.6. For coatings having a dry film thickness up to and including 2.0 mils (50.8 μm), space the cuts 1 mm apart and make six cuts unless otherwise agreed upon.
    1.7. For coatings having a dry film thickness between 2.0 mils (50.8 μm) and 5 mils (127 μm), space the cuts 2 mm apart and make six cuts. For films thicker than 5 mils (127 μm), the method may need to be further modified.
    1.8. Make all cuts about 20 mm (¾ in.) long. Cut through the film to the substrate in one steady motion using just sufficient pressure on the cutting tool to have the cutting edge reach the substrate. When making successive single cuts with the aid of a guide, place the guide on the uncut area.
    1.9. After making the required cuts brush the film lightly with a soft brush or tissue to remove any detached flakes or ribbons of coatings.
    1.9.1. Note: wear cut resistant gloves on the non-cutting hand.
    1.10. Examine the cutting edge and, if necessary, remove any flat spots or wire-edge by abrading lightly on a fine oil stone. Make the additional number of cuts at 90° to and centered on the original cuts.
    1.11. Brush the area as before and inspect the incisions for reflection of light from the substrate. If the substrate surface has not been reached make another grid in a different location.
    1.12. At initiation of testing, remove two complete layers from the roll of tape and discard. Remove an additional length at a steady (i.e. not jerked) rate and cut a piece about 75 mm (3 in.) long.
    1.13. Place the center of the tape over the grid, and in the area of the grid smooth into place by a finger. To ensure good contact with the film rub the tape firmly with an eraser on the end of a pencil or the like. If a colorant is used in the formulation, the color under the tape is a useful indication of when good contact has been made.
    1.14. Within 90+/−30 s of application, remove the tape by seizing the free end and rapidly (but not jerked) back upon itself at as close to an angle of 180° as possible.
    1.15. Inspect the grid area for removal of coating from the substrate using an illuminated magnifier. Rate the adhesion in accordance with the scale illustrated in ASTM D3359-09 Test Method B FIG. 1.
2. Reporting of Test Results
    2.1. Report the substrate material.
    2.2. Report the coating formulation and coating weight of each sample.
    2.3. Report the brand, model, and the lot of the pressure sensitive tape used.
    2.4. Report the orientation of the coating on the substrate (i.e., cathode side of battery canister).

2.5. Report the number of test samples measured, their mean score, and the range of scores for each sample.

All other disclosures in ASTM D3359-09, Test Method B, were followed in order to test the adhesion strength of the coatings disclosed herein.

Dissolution Test

The methods used to test the percent dissolution of the coatings in the disclosure herein follow the procedure described below. If the formulation of the coating composition does not include a colorant, said coating composition should be doped with a colorant, for example, FD&C Blue #1, then proceed to begin the Dissolution Test below. The procedure and reporting methods are described herein:
1. Preparation and Testing of Samples
   1.1.1. Coat a known mass of solution onto an article having a surface (e.g. metal surface of a battery) using a scale.
   1.1.2. Dry the coating in a 65° C. oven for 30 minutes until the coating is dry.
   1.1.3. Allow the article to equilibrate in a 23° C., 35% relative humidity (RH) environment.
      1.1.3.1. Measure the moisture of the dry coating material at equilibrium.
      1.1.3.2. Record the equilibrium moisture.
      1.1.3.3. Record the mass of the coated article (e.g. battery).
   1.1.4. Fill a beaker with 100 mL of deionized (DI) water, inherently at a pH of about 7, at 23° C.±2° C.
   1.1.5. Set timer to t=0.
   1.1.6. Lower the coated article into the beaker, e.g. using a magnetic stick.
      1.1.6.1. Be sure to position the article in the beaker so that the coated side is facing up, and away from the wall of the beaker.
   1.1.7. At 10 seconds, gently remove the coated article from the water, e.g. using a magnet.
      1.1.7.1. If the article is a battery, attach a magnet to the coated side of the battery.
      1.1.7.2. Avoid scraping the coating on the beaker.
   1.1.8. Homogenize the solution remaining in the beaker by mixing with a stir bar.
   1.1.9. Place five aliquots of solution into crystal cuvettes.
   1.1.10. Measure absorbance of the aliquot at a wavelength the colorant in the coating absorbs at, for example 629.0 nm.
      1.1.10.1. 629.0 nm is the wavelength associated with FD&C Blue #1.
      1.1.10.2. Record the absorbance values for the aliquots.
2. Reporting of Test Results
   2.1. Input the absorbance values into the linear regression equation (Beer's law, Absorbance=$\varepsilon bc$ wherein $\varepsilon$ is a wavelength-dependent absorptivity coefficient, b is the path length, and c is the analyte concentration) to find correlated concentration of solution.
   2.2. Calculate the absolute mass of the coating in the solution.
      2.2.1. Concentration times volume of water in the beaker=absolute mass.
   2.3. Calculate the exposed area of the coating. This is equal to the total possible mass of coating that can dissolve.
      2.3.1. If using a circular magnet to lower and raise the sample, this equates to area of the magnet divided by coated surface area times the total coating mass, for example, 7.5 mm$^2$/10 mm$^2$×0.0375 g=0.0232 g exposed mass of coating maximum.
   2.4. Calculate the % dissolution; this equates to the absolute mass of coating dissolved divided by the maximum exposed coating mass times 100.

EXAMPLES

In the following Examples 1-73, coating compositions comprising PVOH, PAA or a combination thereof were formulated. Each of Examples 1-73 in Table 1 included a PVOH resin as the sole resin, a PAA as the sole resin, or a blend of PVOH and PAA. The weight ratio of PVOH to PAA is provided in Table 1, below. Table 1 further indicates the viscosity and degree of hydrolysis for the PVOH resins and the weight average molecular weight of the PAA resin. The PVOH of Examples 7, 14, 21, 28, 35, 42, 49, 56, and 63 were PVOH/maleic anhydride copolymers. The PVOH of all other PVOH-containing Examples were homopolymers. The PAA of all PAA-containing Examples were homopolymers.

The Examples in Table 1 were formulated as such: the PVOH resin, when present, was included in an amount of 15 g (100% PVOH), 11.25 g (75% PVOH), 7.50 g (50% PVOH), or 3.75 g (25% PVOH); the PAA resin, when present, was included in an amount of 3.75 g (25% PAA), 7.50 g (50% PAA), 11.25 g (75% PAA) or 15.0 g (100% PAA); 0.11 g of an aversive agent (denatonium benzoate) in propylene glycol, 14.83 g of a colorant (FD&C Blue #1), 0.06 g of an anti-foaming agent, and 85.0 g of water.

Examples 1-73 were applied to a nickel coated stainless steel battery by pipette and were tested for average adhesion and average percent dissolution. The coating compositions were applied as single layer coatings. The adhesion values were measured according to modified ASTM D3359-09 method (Adhesion Test), described above, and are provided in Table 1. An average adhesion value on a scale from 0-5 was given to each dried coating composition of Examples 1-73, wherein a higher adhesion value indicated greater adhesion to the substrate and a lower adhesion value indicated poor adhesion to the substrate. The average percent dissolution values were measured according to the Dissolution Test, described above, and are provided in Table 1.

TABLE 1

| Examples | Ratio of PVOH to PAA | PVOH Viscosity (in cP) | PVOH DH % | PAA $\overline{M}w$ (in Da) | Average Adhesion Value | Average Percent Dissolution |
|---|---|---|---|---|---|---|
| 1 | 100:0 | 4 | 88 | 0 | 1.5 | 19.661** |
| 2 | 100:0 | 8 | 88 | 0 | 0 | 15.953 |
| 3 | 100:0 | 23 | 88 | 0 | 0 | 15.477 |
| 4 | 100:0 | 15 | 79 | 0 | 1 | 15.400 |
| 5 | 100:0 | 4 | 98 | 0 | 1 | 20.378** |
| 6 | 100:0 | 18 | 80 | 0 | 0 | 11.246 |
| 7 | 100:0 | 17.5 | 90 | 0 | 0 | 14.641 |
| 8 | 75:25 | 4 | 88 | 2,000 | 3* | 17.419** |

TABLE 1-continued

| Examples | Ratio of PVOH to PAA | PVOH Viscosity (in cP) | PVOH DH % | PAA $\overline{M}w$ (in Da) | Average Adhesion Value | Average Percent Dissolution |
|---|---|---|---|---|---|---|
| 9 | 75:25 | 8 | 88 | 2,000 | 2* | 20.229** |
| 10 | 75:25 | 23 | 88 | 2,000 | 1.5* | 16.918** |
| 11 | 75:25 | 15 | 79 | 2,000 | 3* | 19.348** |
| 12 | 75:25 | 4 | 98 | 2,000 | 1* | 19.302** |
| 13 | 75:25 | 18 | 80 | 2,000 | 2* | 15.633 |
| 14 | 75:25 | 17.5 | 90 | 2,000 | 3* | 17.385** |
| 15 | 75:25 | 4 | 88 | 100,000 | 3* | 21.084** |
| 16 | 75:25 | 8 | 88 | 100,000 | 3* | 14.534 |
| 17 | 75:25 | 23 | 88 | 100,000 | 3.5* | 13.618 |
| 18 | 75:25 | 15 | 79 | 100,000 | 3* | 18.140** |
| 19 | 75:25 | 4 | 98 | 100,000 | 2* | 19.399** |
| 20 | 75:25 | 18 | 80 | 100,000 | 3.5* | 14.160 |
| 21 | 75:25 | 17.5 | 90 | 100,000 | 2.5* | 15.661 |
| 22 | 75:25 | 4 | 88 | 250,000 | 3* | 19.385** |
| 23 | 75:25 | 8 | 88 | 250,000 | 3* | 18.613** |
| 24 | 75:25 | 23 | 88 | 250,000 | 3.5* | 11.668 |
| 25 | 75:25 | 15 | 79 | 250,000 | 3* | 16.192 |
| 26 | 75:25 | 4 | 98 | 250,000 | 2* | 12.708 |
| 27 | 75:25 | 18 | 80 | 250,000 | 3* | 11.672 |
| 28 | 75:25 | 17.5 | 90 | 250,000 | 5* | 14.255 |
| 29 | 50:50 | 4 | 88 | 2,000 | 4* | 27.484** |
| 30 | 50:50 | 8 | 88 | 2,000 | 3.5* | 18.436** |
| 31 | 50:50 | 23 | 88 | 2,000 | 3* | 18.032** |
| 32 | 50:50 | 15 | 79 | 2,000 | 3* | 16.229 |
| 33 | 50:50 | 4 | 98 | 2,000 | 2.5* | 19.430** |
| 34 | 50:50 | 18 | 80 | 2,000 | 3* | 15.696 |
| 35 | 50:50 | 17.5 | 90 | 2,000 | 2* | 20.201** |
| 36 | 50:50 | 4 | 88 | 100,000 | 3* | 18.397** |
| 37 | 50:50 | 8 | 88 | 100,000 | 4* | 17.702** |
| 38 | 50:50 | 23 | 88 | 100,000 | 3* | 17.479** |
| 39 | 50:50 | 15 | 79 | 100,000 | 3* | 13.227 |
| 40 | 50:50 | 4 | 98 | 100,000 | 3* | 18.048** |
| 41 | 50:50 | 18 | 80 | 100,000 | 2.5* | 9.760 |
| 42 | 50:50 | 17.5 | 90 | 100,000 | 3* | 15.061 |
| 43 | 50:50 | 4 | 88 | 250,000 | 3* | 17.330** |
| 44 | 50:50 | 8 | 88 | 250,000 | 2.5* | 16.380 |
| 45 | 50:50 | 23 | 88 | 250,000 | 2.5* | 13.304 |
| 46 | 50:50 | 15 | 79 | 250,000 | 2* | 12.391 |
| 47 | 50:50 | 4 | 98 | 250,000 | 3* | 14.054 |
| 48 | 50:50 | 18 | 80 | 250,000 | 3* | 12.784 |
| 49 | 50:50 | 17.5 | 90 | 250,000 | 3* | 16.885** |
| 50 | 25:75 | 4 | 88 | 2,000 | 3* | 22.073** |
| 51 | 25:75 | 8 | 88 | 2,000 | 2* | 17.531** |
| 52 | 25:75 | 23 | 88 | 2,000 | 2.5* | 24.808** |
| 53 | 25:75 | 15 | 79 | 2,000 | 2* | 27.425** |
| 54 | 25:75 | 4 | 98 | 2,000 | 3* | 28.244** |
| 55 | 25:75 | 18 | 80 | 2,000 | 2* | 21.181** |
| 56 | 25:75 | 17.5 | 90 | 2,000 | 1* | 29.782** |
| 57 | 25:75 | 4 | 88 | 100,000 | 2* | 16.693** |
| 58 | 25:75 | 8 | 88 | 100,000 | 3* | 17.028** |
| 59 | 25:75 | 23 | 88 | 100,000 | 2.5* | 13.492 |
| 60 | 25:75 | 15 | 79 | 100,000 | 2* | 13.966 |
| 61 | 25:75 | 4 | 98 | 100,000 | 3* | 17.715** |
| 62 | 25:75 | 18 | 80 | 100,000 | 4* | 13.527 |
| 63 | 25:75 | 17.5 | 90 | 100,000 | 3* | 19.497** |
| 64 | 25:75 | 4 | 88 | 250,000 | 3* | 15.330 |
| 65 | 25:75 | 8 | 88 | 250,000 | 3* | 14.028 |
| 66 | 25:75 | 23 | 88 | 250,000 | 3* | 9.164 |
| 67 | 25:75 | 15 | 79 | 250,000 | 2* | 17.950** |
| 68 | 25:75 | 4 | 98 | 250,000 | 2* | 13.385 |
| 69 | 25:75 | 18 | 80 | 250,000 | 2* | 12.376 |
| 70 | 25:75 | 17.5 | 90 | 250,000 | 2* | 9.624 |
| 71 | 0:100 | | | 2,000 | 0 | 32.088** |
| 72 | 0:100 | | | 100,000 | 1 | 12.931 |
| 73 | 0:100 | | | 250,000 | 2 | 13.480 |

*Denotes synergistic effect
**Denotes average % dissolution of about 17 or greater The adhesion values in Table 1 indicated the presence of a synergistic effect between PVOH and PAA on the adhesion values of the coatings. Examples 8-70 including a combination of PVOH and PAA had improved adhesion values relative to Examples 1-7 (PVOH as the sole resin) and Examples 71-73 (PAA as the sole resin), demonstrating an unexpected advantage of the blend of PVOH and PAA when adhering the dried coating compositions to a metal surface of a substrate. In particular, an unexpected synergistic effect is present for a PVOH/PAA resin blend when the average adhesion value of the blend is greater than that of the weighted average of the two individual resins. For example, if a dried coating composition including a PVOH resin as the sole resin had an adhesion value of 0 and a dried coating composition including a PAA resin as the sole resin had an adhesion value of 1, the expected adhesion value for a 50:50 blend of the PVOH resin and PAA resin was the weighted average of the individual adhesion values, or 0.5.

Unexpectedly, a synergistic effect on adhesion to a metal surface of a substrate was demonstrated for all dried coating compositions including a blend of PVOH and PAA, for example, by comparing Example 1 (100% PVOH 4-88), Example 71 (100% PAA, 2,000 Da) and Example 29 (PVOH 4-88/PAA 2,000 Da blend). As shown in Table 1, the coating of Example 1 gave an average adhesion value of 1.5 and the coating of Example 71 gave an average adhesion value of 0. Thus, prior to the results described herein, the expectation would have been that a blend of the resins of Examples 1 and 71 would result in a coating giving an adhesion value of 0.75 based on the weighted average calculation of the two individual resins. Unexpectedly, it was found that a coating including a blend of the two resins, e.g. Example 29 (50:50 ratio), had a significantly improved average adhesion value of 4, demonstrating the synergistic effect between the PVOH and PAA when blended.

Similar synergistic effects can be seen by a comparison of Examples 2, 72 and 37. Example 2 (100% PVOH 8-88) and Example 72 (100% PAA, 100,000 Da) have poor average adhesion values of 0 and 1, respectively. However, a 50:50 blend of PVOH 8-88 and PAA 100,000 Da (Example 37) showed a significant improvement in average adhesion value (the average adhesion value of Example 37 was 4). The synergistic effect can further be seen by a comparison of Examples 7, 73, and 28. Example 7 (100% PVOH 17.5-90) and Example 73 (100% PAA 250,000 Da) have poor adhesion values of 0 and 2, respectively. However, a 75:25 blend of PVOH 17.5-90 and PAA 250,000 Da (Example 28), once again showed a significant improvement in average adhesion value (the average adhesion value of Example 28 was 5). Thus, Table 1 shows that dried coating compositions of the disclosure, including a water-soluble resin mixture including a PVOH resin and a PAA resin advantageously and significantly improves the average adhesion value of the resulting coating, relative to a coating prepared from a comparative dried coating composition which is identical but for including a sole resin and the amount of that sole resin in the comparative dried coating composition being equal to the total amount of resin in the resin blend coating compositions.

The percent dissolution of the dried coating compositions was also measured and is shown in Table 1. The dissolution percentage can correlate to the rate of release/transfer of colorant and/or aversive agent from the coatings of the disclosure when the coatings of the disclosure are contacted with moisture, e.g. in the mouth of a child. For example, a coating of the disclosure that has a high dissolution percent will dissolve faster when in contact with a wet environment, relative to a coating of the disclosure having a low dissolution percent, thereby advantageously releasing colorant and/or aversive agent more effectively to a location.

Advantageously, the coating compositions of the disclosure can be designed to have one or more benefits, including, but not limited to, the ability to form coatings having improved adhesion to a metal surface of a substrate, fast rates of release/transfer of a colorant and/or aversive agent to, for example, a soft tissue, or a combination thereof. As shown in Table 1, coatings of the disclosure can advantageously demonstrate both good adhesion (e.g., adhesion values of 3 or more) and good rates of release/transfer of colorant/aversive agent (e.g., percent dissolutions of about 10 or more). Although, the coatings of the disclosure are indicated to have good rates of release/transfer of colorant/aversive agent at a percent dissolution of 10 or more, the coatings of the disclosure are indicated to have excellent rates of release/transfer of colorant/aversive agent at a percent dissolution of 17 or more. For example, the coating compositions of the disclosure comprising a PVOH and a PAA present in a weight ratio in a range of about 50:50 to 75:25, respectively, wherein the PVOH has a viscosity of less than 8 cP and a DH of less than 98% advantageously demonstrate adhesion values of 3 or more and percent dissolution values of about 17 or more. Additionally, coating compositions of the disclosure comprising PVOH and PAA present in a weight ratio of about 50:50, wherein the PVOH has a DH of less than 90% and the PAA has a $\overline{M}w$ of about 1,000 Da to about 200,000 Da, demonstrate adhesion values of 3 or more and percent dissolution values of about 17 or more.

Example 74: Electrical Resistance Test

A nickel-coated stainless steel button/coin battery (battery) is attached to a ohmmeter and the electrical resistance is tested. The ohmmeter is removed for about 1 minute to about 10 minutes, the ohmmeter is reattached, and the electrical resistance is again tested. The ohmmeter is again removed for about 1 minute to about 10 minutes, the ohmmeter is reattached, and the electrical resistance is tested for a third time. An average of the three values is taken. The battery is then coated by a known mass of coating composition described herein, the mass is then recorded using a scale. The coating composition is applied wherein the coating composition does not cover the entire surface of the battery, such as in a ring shape described above, and/or the coating composition comprises electrical conductors. The coating composition is dried to the point wherein the residual moisture content of the dried coating composition is between 1% and 10%, such as between 1% and 6%. The dried coating composition, i.e., the coating, is no thicker than 2 mil. The coated battery is then equilibrated to room temperature, 23° C.±2° C. The mass of the coated battery is recorded using a scale. The coated battery is attached to an ohmmeter and the electrical resistance is tested. The ohmmeter is removed for about 1 minute to about 10 minutes, the ohmmeter is reattached, and the electrical resistance is again tested. The ohmmeter is again removed for about 1 minute to about 10 minutes, the ohmmeter is reattached, and the electrical resistance is tested for a third time. An average of the three values is taken. In embodiments, the electrical resistance of the coated battery according to the Electrical Resistance Test is ±1% of the resistance of the battery before the dried coating composition is coated on the battery.

The foregoing description is given for clearness of understanding only, and no unnecessary limitations should be understood therefrom, as modifications within the scope of the invention may be apparent to those having ordinary skill in the art.

All patents, publications and references cited herein are hereby fully incorporated by reference. In case of conflict between the present disclosure and incorporated patents, publications and references, the present disclosure should control.

What is claimed:

1. A coating composition, comprising:
a water-soluble resin mixture comprising
   (a) a polyvinyl alcohol (PVOH) comprising a polyvinyl alcohol homopolymer, a polyvinyl alcohol copolymer having an anionic modification, or a combination thereof, and having a 4% solution viscosity at 20° C. of about 25 cP or less and a polyacrylic acid (PAA) homopolymer having a weight average molecular weight ($\overline{M}w$) in a range of 1000 Da to 300,000 Da, wherein the PVOH and PAA are in a ratio in a range of 80:20 to 20:80 by weight, respectively; and
   (b) an aversive agent comprising a denatonium salt, sucrose octaacetate, quinine, a flavonoid, a quassinoid, or a combination thereof.

2. A coating composition, comprising:
a water-soluble resin mixture comprising
   (a) a polyvinyl alcohol (PVOH) comprising a polyvinyl alcohol homopolymer, a polyvinyl alcohol copolymer having an anionic modification, or a combination thereof, and having a 4% solution viscosity at 20° C. of about 25 cP or less and a polyacrylic acid (PAA) homopolymer having a weight average molecular weight ($\overline{M}w$) in a range of 1000 Da to 300,000 Da, wherein the PVOH and PAA are in a ratio in a range of 80:20 to 20:80 by weight, respectively; and
   (b) a colorant comprising a triphenylmethane dye, an azo dye, an anthraquinone dye, a perylene dye, an indigoid dye, a food, drug and cosmetic (FD&C) colorant, an organic pigment, an inorganic pigment, or a combination thereof, wherein the colorant is at a concentration±10% of the saturation point of the colorant.

3. The coating composition of claim 1, wherein the PVOH is a PVOH homopolymer.

4. The coating composition of claim 1, wherein the aversive agent comprises denatonium benzoate (DnBz) and the DnBz concentration is in a range of 1,000 to 20,000 ppm based on the total weight of the coating composition.

5. The coating composition of claim 1, wherein the coating composition further comprises a colorant.

6. The coating composition of claim 5, wherein the colorant comprises a triphenylmethane dye, an azo dye, an anthraquinone dye, a perylene dye, an indigoid dye, a food, drug and cosmetic (FD&C) colorant, an organic pigment, an inorganic pigment, or a combination thereof.

7. The coating composition of claim 5, wherein the coating composition comprises water and the colorant is present in an amount of at least 15 parts colorant to 70 parts water.

8. The coating composition of claim 1, wherein the coating composition comprises a colorant present in greater than or equal to 17% by weight of the solids content.

9. A coating, comprising:
a first water-soluble layer comprising the coating composition according to claim 1 that is dried first.

10. The coating of claim 9, further comprising a second water-soluble layer comprising a dried second coating composition.

11. The coating of claim 10, wherein the dried second coating composition is free of colorants.

12. The coating of claim 10, wherein the dried second coating composition comprises a water-soluble polymer and the water-soluble polymer comprises a PVOH having a 4% solution viscosity at 20° C. of no more than about 10 cP.

13. The coating of claim 10, wherein the dried second coating composition further comprises a plasticizer.

14. The coating of claim 13, wherein the weight ratio of the PVOH of the dried second coating composition to plasticizer is about 4:1.

15. The coating of claim 14, wherein the plasticizer of the dried second coating comprises glycerol, polyethylene glycol, propylene glycol, monoacetin, triacetin, triethyl citrate, sorbitol, 1,3-butanediol, D-glucono-1,5-lactone, or a combination thereof.

16. The coating of claim 9, wherein the first water-soluble layer is provided on a surface of a substrate.

17. The coating of claim 9, wherein the coating has an adhesion value of 3 or greater when coated on a nickel coated stainless steel substrate, according to the Adhesion Test.

18. The coating of claim 9, wherein the coating has an average dissolution percent of about 17 or more according to the Dissolution Test.

19. The coating of claim 9, wherein the coating has a thickness of no greater than 1 mil (25.4 μm).

20. A method for applying the coating composition of claim 1 to a surface of a substrate, the method comprising:
contacting the surface of the substrate with the coating composition.

21. The method of claim 20, wherein the substrate comprises nickel coated stainless steel, aluminum coated steel, zinc coated steel, copper coated steel, tin coated steel, aluminum-zinc alloy, or a combination thereof.

22. The method of claim 20, wherein the coating composition is applied to the surface of a substrate in a design comprising a ring, concentric circles, a matrix of dots, a grid pattern, or a combination thereof.

23. The method of claim 20, wherein contacting the surface of the substrate with the coating composition comprises ink jet printing, needle deposition, dip coating, curtain coating, spray coating, pad printing, gravure printing, reverse gravure printing, or a combination thereof.

24. A method of deterring ingestion of a substrate, comprising applying to a surface of the substrate the coating composition according to claim 1.

25. The method of claim 24, wherein the surface of the substrate comprises metal, plastic, wood, glass, paper, composite, ceramic, stone, or rubber.

26. An article comprising a surface of a substrate, the surface comprising the coating according to claim 9.

27. The article of claim 26, wherein the surface of the substrate comprises metal, plastic, wood, glass, paper, composite, ceramic, stone, or rubber.

28. A kit comprising a substrate, comprising a surface of a substrate coated with the coating composition according to claim 1 and instructions to not wash, rinse, or otherwise contact the substrate surface with water or solvents.

* * * * *